United States Patent
Mielekamp

(10) Patent No.: US 8,055,044 B2
(45) Date of Patent: Nov. 8, 2011

(54) FLEXIBLE 3D ROTATIONAL ANGIOGRAPHY AND COMPUTED TOMOGRAPHY FUSION

(75) Inventor: Pieter Maria Mielekamp, Eindhoven (NL)

(73) Assignee: Koninklijke Philips Electronics N V, Eindhoven (NL)

(*) Notice: Subject to any disclaimer, the term of this patent is extended or adjusted under 35 U.S.C. 154(b) by 1212 days.

(21) Appl. No.: 11/573,576

(22) PCT Filed: Aug. 4, 2005

(86) PCT No.: PCT/IB2005/052608
§ 371 (c)(1),
(2), (4) Date: Feb. 12, 2007

(87) PCT Pub. No.: WO2006/018774
PCT Pub. Date: Feb. 23, 2006

(65) Prior Publication Data
US 2008/0304615 A1  Dec. 11, 2008

(30) Foreign Application Priority Data
Aug. 17, 2004 (EP) .................... 04103935

(51) Int. Cl.
*G06K 9/00* (2006.01)
(52) U.S. Cl. .................... 382/130
(58) Field of Classification Search .............. 382/130
See application file for complete search history.

(56) References Cited

U.S. PATENT DOCUMENTS

| | | | |
|---|---|---|---|
| 5,690,106 A | 11/1997 | Bani-Hashemi et al. | |
| 5,782,762 A * | 7/1998 | Vining | 600/407 |
| 5,832,134 A | 11/1998 | Avinash et al. | |
| 5,852,646 A | 12/1998 | Klotz et al. | |
| 6,999,811 B2 * | 2/2006 | Koppe et al. | 600/426 |
| 2003/0021381 A1 | 1/2003 | Koppe et al. | |
| 2003/0053697 A1* | 3/2003 | Aylward et al. | 382/203 |
| 2003/0088179 A1 | 5/2003 | Seeley et al. | |
| 2003/0194121 A1* | 10/2003 | Eberhard et al. | 382/132 |
| 2003/0208116 A1 | 11/2003 | Liang et al. | |
| 2004/0030246 A1 | 2/2004 | Townsend et al. | |

FOREIGN PATENT DOCUMENTS

| | | |
|---|---|---|
| DE | 3931531 A1 | 4/1990 |
| EP | 0919185 A1 | 6/1999 |
| EP | 1081647 A1 | 3/2001 |

* cited by examiner

*Primary Examiner* — Hadi Akhavannik

(57) ABSTRACT

One of two data sets, originating from two different radiological methods is processed to generate interim results, yielded by an operation on one of the data sets. The interim results are used to modify the other data set. Different imaging capabilities of the employed radiological methods promote a particular task, e.g. the segmentation of a given type of tissue. When the combined data of both methods is displayed, clinical users benefit from the complementary information. Care is taken, that only relevant information is presented to the user, as to avoid irrelevant data obscuring any data of interest. Therefore, the data to be displayed is filtered based on content, e.g. the type of tissue, and on location. Three-dimensional computer tomography and three-dimensional rotational angiography are particularly applicable radiological methods.

16 Claims, 5 Drawing Sheets

FLEXIBLE 3D ROTATIONAL ANGIOGRAPHY AND COMPUTED TOMOGRAPHY FUSION

BACKGROUND

The present application relates to imaging systems, particularly diagnostic imaging systems. It finds particular application in conjunction with an integrated three-dimensional rotational angiographic (3DRA) and computerized tomographic (CT) diagnostic imaging system and will be described with particular reference thereto. However, it should be appreciated, that the present application may also find application in conjunction with other types of multi-modality diagnostic imaging systems. The present application-is particularly useful for visualizing blood vessel structures around and inside the skull.

For diagnostical purposes in a clinical environment, the separate visualization of the various represented tissue types when employing a radiological acquisition method can provide useful information about the clinical picture of a patient. With different radialogic methods being specialized on the visualization of one or a few kinds of tissues, the goal of displaying only useful information is normally achieved by choosing the adequate acquisition method. However, some tissue types tend to have similar properties regarding suitable acquisition methods, although their respective function inside the human body is completely different, e.g. blood vessels and bone structure. For the reason of different functions of the tissue concerned, it is desirable to represent them in a distinct manner, either by color coding according to tissue type or by masking all tissue types but the one the operator is interested in. The problem of overlapping property distributions for different types of tissue is particularly present in three-dimensional rotational angiography. In general, in 3DRA no absolute correct density values will be available due to insufficient calibration and reconstruction procedures. In this method, the segmentation of artery/vessel information in the 3DRA volume is hindered by the fact that the artery/vessel densities are in the same range as bone material, due to beam hardening caused by the skull. Furthermore, the high density data of the skull in the CT volume, which is typically used for orientation of the CT slices, prevents a clear view on the arterial structures, when both volumes are combined.

While Computer Tomography (CT) is known to provide high contrast between bony structures and soft tissue (e.g. skull as opposed to brain), the use of three-dimensional rotational angiography (3DRA) for extraction of 3-D vessel information is hindered by the fact, that the intensity distribution of high intensity bone overlaps with the intensity distribution of contrast filled vessels. This effect is especially due to the phenomenon of beam-hardening caused by the skull, in combination with insufficient calibration and reconstruction procedures.

U.S. Pat. No. 5,832,134 to Avinash and Alyassin discloses a method for removing dominating structures for enhancing visualization of desired structures that circumvents the time consuming human-operator interaction. The basic idea of the application disclosed therein is to distinguish between highly connected regions on the one hand and more weakly connected regions. Regions, that are strongly connected correspond to bony structures, whereas regions, that are less strongly connected correspond to vessels. The introduction of this property makes available a new feature for an improved automatic segmentation of unwanted bone structure from the interesting vessel information. However, the method only interprets the inherently unsuitable data material provided by the three-dimensional rotational angiographic acquisition method in a different manner and does not revert to more suitable information sources. Furthermore, the morphological algorithms described therein, e.g. connectivity analysis, and voxel dilation, depend greatly on an optimal parameterization, which in turn is dependant from geometrical conditions, e.g. acquisition resolution or size of the object.

SUMMARY

Considering the above, it is an object of the application to provide a system and a method for visualization of biological tissue using two acquisition devices for higher information content.

Provided is a system for visualization of biological tissue, according to the 30 application comprising a first device for obtaining a first set of data including information as to a three-dimensional location and as to physical properties in that location, and a second device for obtaining a second set of data including information as to a three-dimensional location and as to physical properties in that location. The system further comprises a data receiving and processing unit connected with the first and second devices for receiving respective sets of data for altering one set of data based on information of the other set of data, and visual output means.

Acquiring an object under different acquisition conditions yields two or more related data sets. Usually, these data sets contain complementary information and one of the data sets may be more appropriate for a given task to be performed. If the object to be visualized is comprised of biological tissue, different acquisition conditions may yield data sets that are particularly well suited for visualizing different types of biological tissue. Besides being visualized, the data sets can be altered during processing. Dependant on what kind of modification on a data set is to be performed, the way, in which the data must be altered for an optimal result, can be determined using the other data set, if that data set contains information, that is well suited for the modification at hand.

The data receiving and processing unit may comprise means for registering both three-dimensional image data sets in particular obtained from the first and second devices, respectively. Means for registration are charged with matching the two data sets with regard to position, size and orientation. Since the two data sets involved usually have different acquisition angles, distances and/or resolutions, registering them is necessary for storing both data sets with regard to a common co-ordinate system. An effective registration is a prerequisite for further data processing.

According to a preferred embodiment of the application, the system comprises means for applying a threshold to and filtering at least one of said data sets situated upstream of said means for registering. The means for registration can yield erroneous results, if the incoming data contains errors. Those errors are usually caused by artefacts originating in the acquisition process. An example of artefacts produced during the acquisition process are voxels that are filled with air, but are assigned a value that indicates a solid matter. If the other acquisition method is less prone to produce such artefacts, or produces different artefacts than those produced by the first acquisition method, then a registration algorithm risks to fail, because it calculates the positions, scales and orientations of the target object in each of the two data sets under the assumption, that the prevailing number of voxels with a high absorption coefficient value are part of the target object. The effectiveness of the means for registration can be restored by a thresholding method. Indeed, when the voxel values outside the skull are set to zero by thresholding on a value between the erroneous air voxel values and the grey matter or brain tissue values, the means for registration deliver data essentially artefact free.

Alternatively, the system may comprise means for identifying a predefined volume in both data sets. These means determine sections of the volumes to be used by upstream registration means, therefore erroneous voxels outside the skull can be discarded.

Preferably, the physical property determined at a particular location can serve for the determination of the type of tissue. Besides determining the range of the target object, the physical property delivers valuable information about the type of tissue present at a particular location. Therefore, the sampled value of a physical property serves for the determination of the type of tissue.

The means for altering preferably uses masking information obtained from located areas of special properties. Once a valid segmentation has been calculated, based on special scanned properties of the tissue, and consequently areas of different types of tissue have been identified, it is possible to mask those areas corresponding to different types of tissue selectively, based on a choice made by an operator of the system. Therefore, this location-dependant tissue type information can be used by downstream means for data processing, such as means for masking certain regions and/or tissues that are of no or little interest for a particular application.

The system may further comprise means for obtaining a sectional view of the first, second and/or a third combined three-dimensional image data set with a preselected geometrical plane. When representing three-dimensional volumes featuring a spacial density of some property via a flat display device, a major problem is the ambiguity of the location of a given point. A human observer usually considers points of reference for orientation, which requires the ability of three-dimensional imagination. A simply shaped sectional view of the data to be displayed can facilitate this task imposed to the user. Another problem is the occultation of areas of interest by those of less interest. For those reasons, displaying too much data becomes counterproductive, even when by definition uninteresting areas are masked out prior to displaying the data.

According to a preferred embodiment, the system further comprises means for rendering data transparent based on location, property, optionally in a preselected volume like a slice. Therefore, a selection of the data, that is actually to be displayed via the means of visualization, can be made. At the same time, a selection of the displaying mode of various kinds of data has to be made as well, one of the modes being transparency. The selection of what data is to be displayed, and at which degree of transparency, is based on location, property, and the shape the section in which data is to be displayed. The display section preferably has a simple geometrical shape, such as a slice or a cube.

Visualization of combined three-dimensional image data sets can be performed along a predefined path, in particular corresponding to a blood vessel. By restricting the volume to be analyzed by a human expert, details are more readily appreciated. However, when ample areas are to be analyzed, a conflict of interests arises. The conflict can be resolved by spreading the observation area over time, i.e. by showing a sequence of related images, each of which is centered around a slightly different location than the preceding ones. To the human expert charged with the interpretation with regard to conspicuous details hinting towards a disease, this sequence appears much like a movie with changing camera position. The sequence of positions defines a path for the movement, that can for example coincide with a blood vessel Furthermore, the application discloses a method for visualization of biological tissue, comprising the steps of:

acquiring a first data set corresponding to a three-dimensional data acquisition based on a first acquisition method;

acquiring a second data set corresponding to three-dimensional data acquisition based on a first acquisition method;

acquiring a second data set corresponding to three-dimensional data acquisition based on a second acquisition method;

extracting information from one of said data sets; and altering the respective other data set based on said extracted information.

The method starts with the acquisition of two data sets, produced by two suitable acquisition methods for the scanning of three-dimensional volumes. Taking advantage of the different imaging characteristics of various acquisition methods, the method extracts information concerning a property to be examined from the one of the two data sets that represents more clearly the desired property and makes this information available for the respective other data set. Based on the extracted information, the method is capable to alter the respective other data set. This is particularly useful for masking or hiding specific regions, if, based on the respective other data set alone, these regions to be hidden cannot be clearly distinguished from regions that are not to be hidden, for the corresponding acquisition method has a lower level of selectivity for the tissues involved.

According to a preferred embodiment, the method proceeds in a succeeding step with the registration of the data sets, i.e. calibrating the data sets with respect to position, orientation and scale. Preferably, this step is performed after the step of acquiring a second data set and prior to the information extraction step.

The method's first acquisition method preferably is a computer tomographic method. Computer tomography (CT) is typically used for the visualization of low contrast soft tissue such as brain material.

The method's second acquisition method preferably is a three-dimensional rotational angiographic method. Three-dimensional rotational angiography (3DRA) is effectively used for visualization of high contrast artery/vessel structures.

Other radiological and non-radiological methods can benefit from the method described herein, as well.

The method may further comprise the step of applying a threshold to and filtering of the three-dimensional rotational angiography data prior to the step of registering the two data sets. In order to avoid deficient registration results, data can be preconditioned prior to the step of registration. Possible preconditioning comprises applying a threshold to the values of the acquired physical property in order to recognize voxels, that fell victim to acquisition principle caused artefact occurrence.

A preferred method further comprises a step of identifying a predefined evaluation volume in both data sets and returning a corresponding subset to said registration means for subsequent registration prior to the step of registering the two data sets. This preconditioning comprises limiting the valid volume for registration to a volume that is known to mainly contain relevant target object information that is, up to a certain extend, represented similarly in both data sets. Indeed, only a fraction of the entire volume has to be examined for registration purposes, if it can be guaranteed, that the relation between the two data sets is rigid, i.e. can be described by means of an affine transformation.

The method according to a preferred embodiment further comprises a step of obtaining a sectional view of the first, second and/or a combination of both three-dimensional image data sets with a preselected geometrical plane. In order for a human expert to analyze the acquired data, it has to be displayed. The interpretation of the displayed volume data is greatly facilitated, when a sectional view of the data is provided in a meaningful manner, i.e. uninteresting parts of the volume are cut away by the section along a preselected geometrical plane.

The method may further comprise a step of rendering data transparent based on location, characteristic and/or sectional view. A possibility to deal with data, that should be displayed, e.g. in order to enable the human observer to orient himself, but does not constitute the most important data to be visualized, is to render the respective areas transparent up to a certain degree. By doing so, more relevant data is still visible through the partly transparent parts of the rendered volume. The decision, which parts of the volume are to be rendered partly transparent is based on location, characteristic, sectional view and other possible properties.

Preferably, the method further comprises the step of displaying the combined three-dimensional data set along a predefined path, in particular a blood vessel. Consequently, the method provides a way to visualize ample volumes without sacrificing easy visual interpretation by displaying a sequence of sectional views, each view centered around a different location, that is part of a predefined path. The path can for example correspond to a blood vessel, so that a human observer has the impression of traveling along this particular blood vessel. The vessel being visualized together with the volume in its vicinity provides an efficient way of representing large quantities of data for downstream expert evaluation.

Merging data originating from different acquisition methods for analysis and visualization, each acquisition method being particularly qualified for a distinct diagnostical task and/or type of tissue, has the advantage that all methods benefit from interim results determined by a method, that is particularly well suited for a particular, required operation.

BRIEF DESCRIPTION OF THE DRAWINGS

These and other aspects of the application will become apparent from and elucidated with reference to preferred embodiments described hereinafter with reference to the accompanying drawings, wherein.

DETAILED DESCRIPTION

The present application is a system and method for flexible fusion of two data sets representing three-dimensional densities of a physical properties. According to a preferred embodiment of the present application, two data sets, which both represent the same object, but were generated using different acquisition methods, are combined in such a way, that the advantages of a particular acquisition method can be of use for a data set that was acquired using a different radiological method. For sake of clarity, the present application is explained here with reference to a preferred embodiment employing two diagnostical radiological methods in particular, these two methods being three-dimensional rotational angiography (3DRA) on the one hand and computer tomography (CT) on the other hand. CT is typically used for visualization of low contrast soft tissue such as brain material, while 3DRA is effectively used for visualization of high contrast artery/vessel structures. Since 3DRA and CT volumes provide complementary information to the clinical users, it is desirable to present this information to them as effectively as possible.

Figure 1:
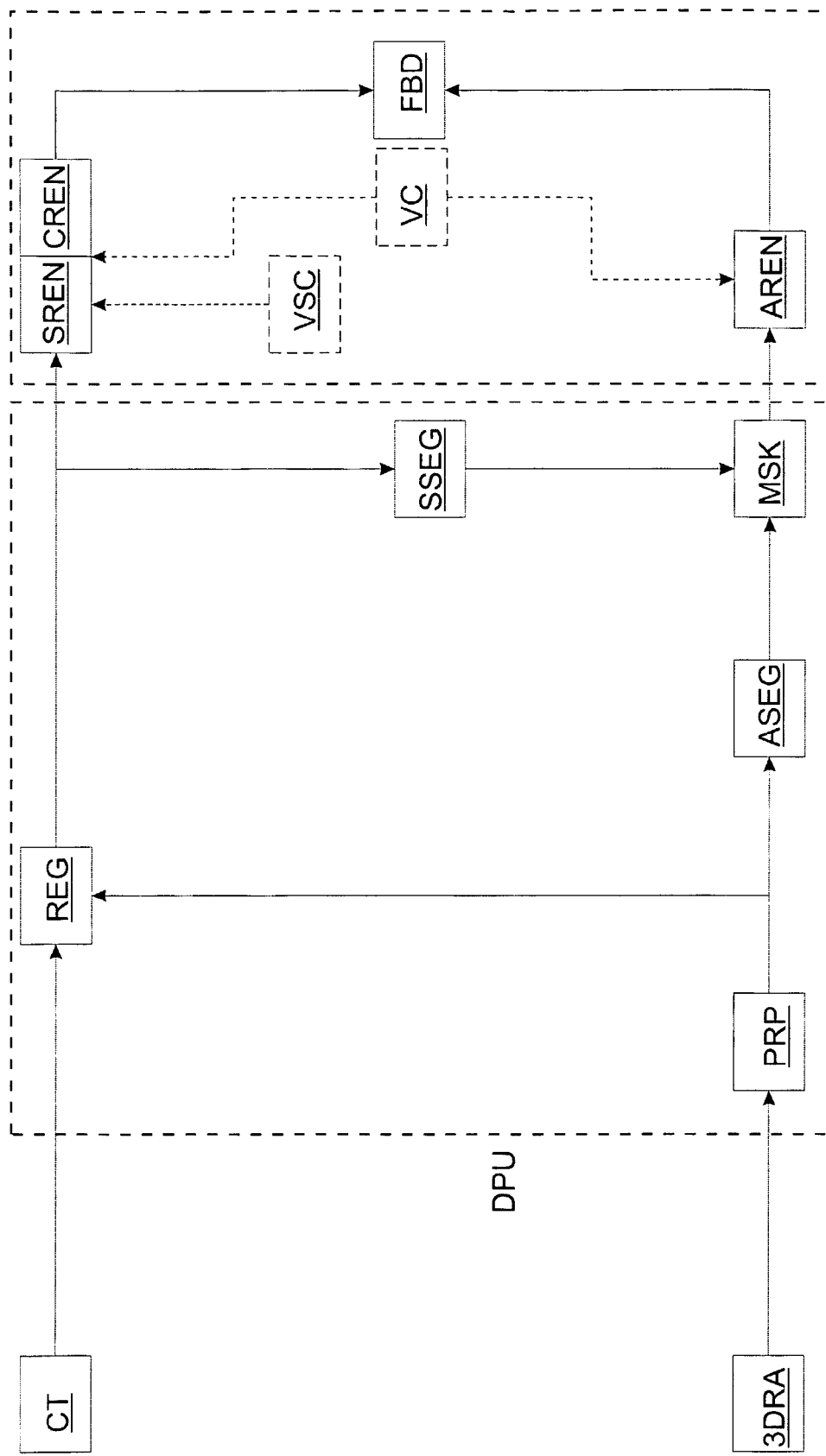
FIG. 1 is a block diagram of a system according to a preferred embodiment of the application.

Referring to FIG. 1, using a computer tomography acquisition device CT, a data set corresponding to the three-dimensional spacial distribution of a physical property inside an examination volume is acquired. In the case of CT, the physical property is the attenuation coefficient with regard to x-rays. The same object, which in a clinical environment is usually a patient, undergoes a second acquisition, this time using a 3DRA acquisition device 3DRA. This technique relies on the same physical principle, namely measuring the attenuation coefficient distribution with regard to x-ray radiation, but differs from CT in the shape of the sensor and the acquisition geometry. In particular, 3DRA employs a central projection onto a two-dimensional radiation detector, whereas CT uses substantially one-dimensional detector arrays. 3DRA datasets generally do not contain absolute calibrated density values, due to insufficient calibration and reconstruction procedures. Both acquired data sets are transmitted to a data receiving and processing unit DPU. The data receiving and processing unit DPU receives the two data sets as inputs and forwards them to several sub-units.

With reference to the 3DRA-generated data, the pre-processing unit PRP eliminates unwanted artefacts inherent to the 3DRA technique and improves the performance of downstream data processing units. The pre-processing unit PRP can be incorporated with either the data receiving and processing unit DPU as depicted in FIG. 1 or the 3DRA acquisition device 3DRA.

The pre-processed 3DRA data set is then transmitted to both, an artery/vessel segmentation unit ASEG and a registration unit REG, charged with the registration of the CT data set and the 3DRA data set. The other input for the registration unit REG is supplied with the data set generated by the CT acquisition device CT. The registration unit ensures, that both data sets are placed in a common co-ordinate system in such a manner, that an object contained in both data sets will be located in the same location regarding each data set. In the described embodiment, the 3DRA-generated data set remains constant, while the CT-generated data set is shifted, scaled and rotated in such way, that a maximum of congruence in position, size and orientation is achieved. The accordingly altered CT-generated data set is transmitted to two destinations, one of which is a unit for rendering a transparent volume slice SREN, and the other is a unit for bone/skull segmentation SSEG. The latter proceeds to segmenting skull/bone information from the CT-generated data set, the result of which will be made available to a 3D masking unit MSK. Another input of this unit is provided by the artery segmentation unit ASEG, that has segmented artery/vessel information from the 3DRA-generated data set. Due to the similar acquisition characteristics of artery/vessel tissue and the skull in the case of 3DRA, the segmented artery/vessel information still contains a considerable quantity of voxels corresponding to the skull and bones. The 3D masking unit MSK merges the two data sets provided by unit SSEG and unit ASEG, respectively, in order to blind out any skull information in the 3DRA-generated data set. In particular, the segmented skull/ bone information extracted from the CT-generated data set is used as a mask, applied to the segmented artery/vessel information. Notice that, due to the different voxel densities, straightforward subtraction will not work in general. An interpolation method, taking into account several voxels of the masking information for one voxel of the evaluation data set, or vice versa, depending on the location in the scanned volume of the voxels, has to be considered, instead. The resulting information contains by and large only the desired artery/vessel information.

In order to be able to display this information in an efficient way to clinical users, the data set has to be passed to a 3D rendering unit AREN, being a part of the visual output means VIS. Based on a user selected viewpoint, illumination, the data set to be displayed and other parameters, a view of the 3D data is generated by 3D rendering AREN by a projection onto 2D space. This 2D-projection is suited to be displayed by a frame buffer display FBD.

If the clinical user is further interested in the condition of the surrounding tissue in the vicinity of an observed blood vessel, e.g. to be able to evaluate any correlated symptoms, the system reverts to the CT-generated data, which has better capabilities in this domain. To this end, the same data feeding the skull/bone segmentation unit SSEG is also applied to a unit for transparent volume slice rendering SREN. Since large volumes are difficult for a user, even if well trained, to grasp, it is preferred, that the additionally displayed CT data is rendered in form of a slice or another simple three-dimensional geometric shape. Control of the position, orientation, size, transparency and other properties of the slice is performed by a volume-slice control unit VSC, either automatically or by interpreting commands issued by the user. By rendering the slice or the equivalent geometrical shape transparent, the problem, that the CT image covers a lot of the arterial/vessel information is resolved.

However, transparent rendering will heavily influence the contrast of the CT information, which is clinically unacceptable.

A remedy is to add non transparent, multi-planar reformatting (MPR) rendering of the top or bottom planes to the transparent rendered volume slice, in order to get the required high contrast in these planes. This is achieved by a second unit for rendering, the cap MPR rendering unit CREN. Depending on the view angle, either the top or the bottom plane is rendered non transparent.

The operation of the visual output means VIS is controlled by a viewing control unit VC. Via this means, the user can interact with the system for modifying view point, zoom etc. The user can further place a virtual probe in a specific location, causing the means for visualization to represent the surrounding tissue in the vicinity of the probe location. By letting the clinical users modify the position and/or orientation of the CT slices, relative to the viewing of the artery/vessel structures, they will have a flexible and clear view of the pathologies at hand. For example, the probe can be placed on an artery vessel by a clinical user, who has an insight on the CT information in the plane orthogonal to the direction of flow.

Figure 2:
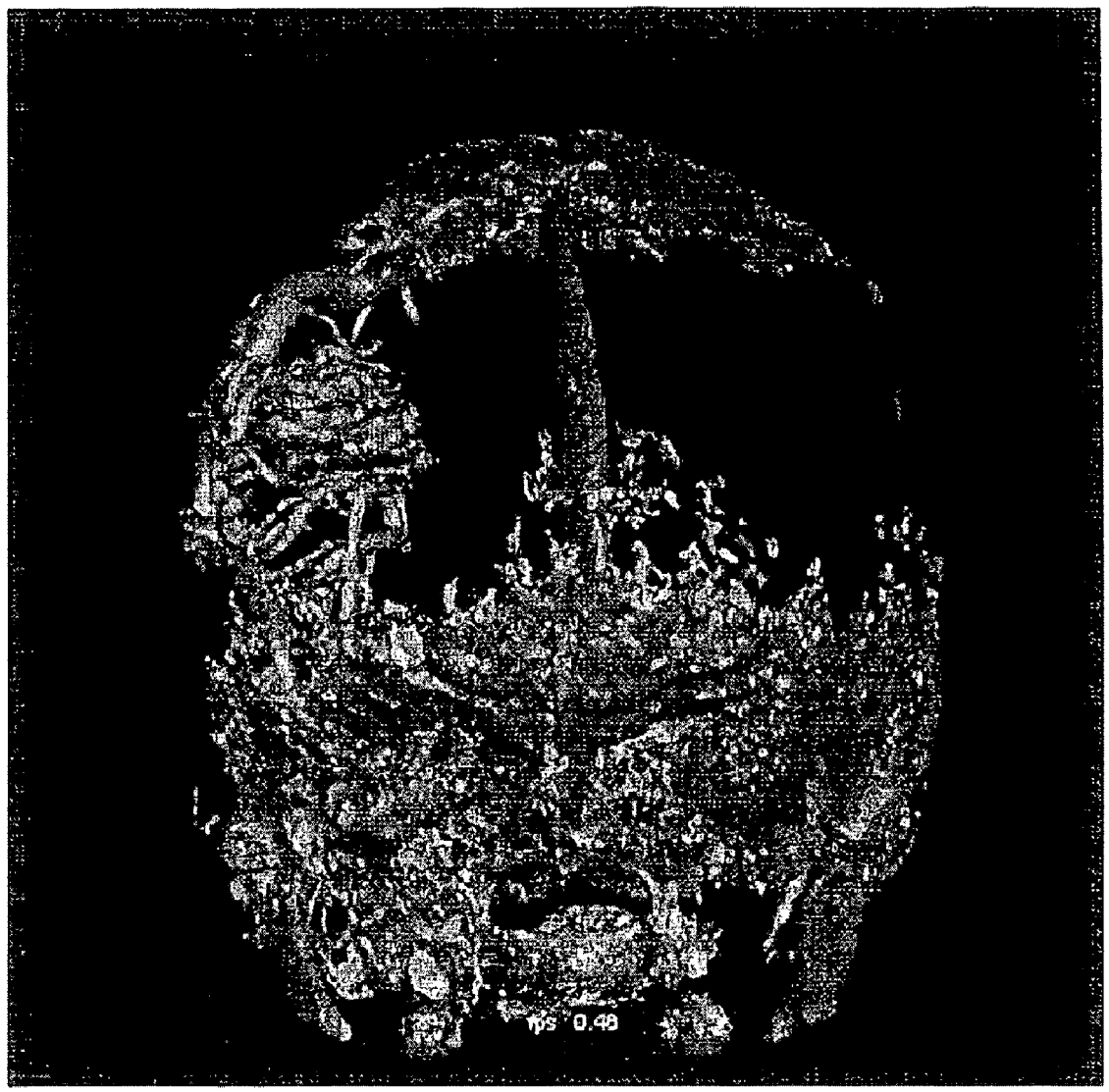
FIG. 2 shows the result of a conventional segmentation of a brain scan as to display artery/vessel information exclusively.

Now with reference to FIG. 2, the result of artery/vessel information based solely on 3DRA data is shown. It becomes apparent, that besides the desired artery/vessel information considerable areas corresponding to the skull are contained in the displayed scan.

Figure 3:
FIG. 3 shows the result of a segmentation of a 3DRA brain scan as described in the application.

Referring now to FIG. 3, the result of masking the segmented artery/vessel data set shown in FIG. 2 with the data set containing the segmented skull, based on the CT image, is represented. It becomes apparent, that a considerable improvement is obtained over segmentation based solely on 3DRA-generated data.

Figure 4:
FIG. 4 shows the result of a segmentation of a brain scan as described in the application of FIG. 3 together with additional computer tomography data, represented as a transparent slice with an opaque bottom.

Now with reference to FIG. 4, a combined 3DRA-CT image is shown, in which a slice containing CT data, and correspondingly representing the skull and soft tissue, is rendered transparent. The bottom plane of this slice, however, is rendered non transparent, as to make more clearly apparent soft tissue. Since a clinical user can adjust the viewpoint, the fact, that some of the 3DRA data is temporarily obscured by the non transparent plane, can easily be dealt with by redefining another viewpoint.

Figure 5:
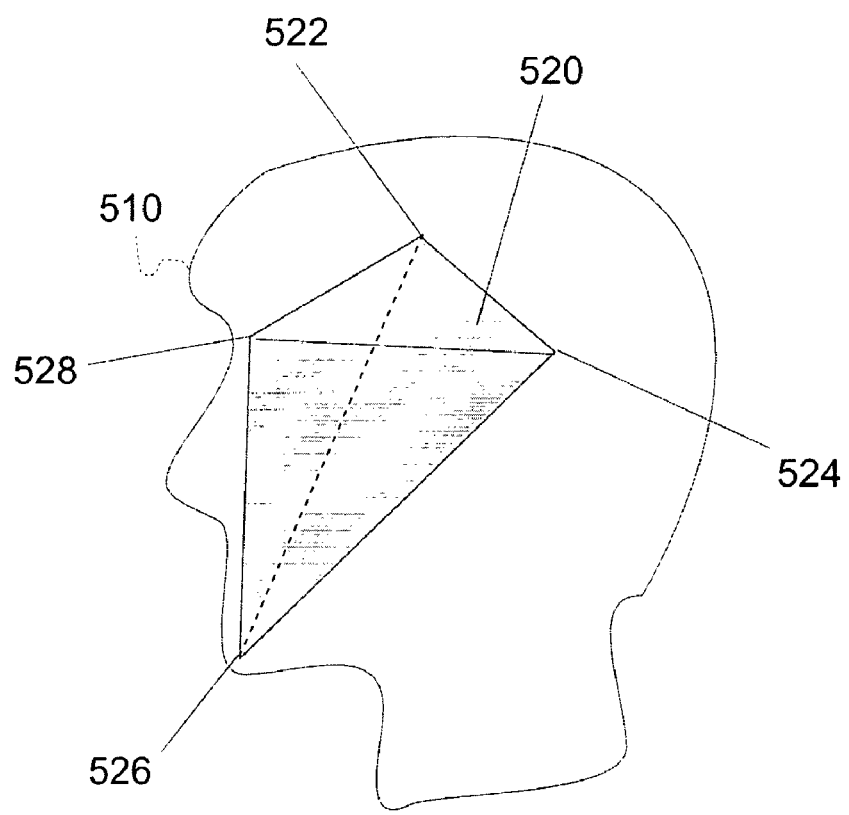
FIG. 5 shows an example of a registration region.

Now with reference to FIG. 5, an example of a region of registration is depicted. In order for the registration to yield high quality results, it is not necessary, that the entire volume is evaluated. It must rather be guaranteed, that unequivocal points of reference can be determined and located in both data sets. These points of reference can either be anatomical landmarks or artificial markers, that are applied to the patient. The location of the points of reference can be determined manually or automatically. Exemplary, FIG. 5 shows a patient's head 510. A simple region to be used for registration is represented by the tetrahedron 520, where each of its four vertices 522, 524, 526, 528 corresponds to an anatomical landmark or a marker. Of course, other shapes can be used as well. In another embodiment, the skull, which usually clearly distinguishable in both kinds of images, can serve as a limiting boundary for the registration region, which generalizes the concept of anatomical landmarks.

In another preferred embodiment, a clinical user can put a probe on an artery/vessel and have an insight on the CT information on the plane orthogonal to the direction of flow.

In another preferred embodiment, the user can, by specifying a begin and end probe, trace through a path being able to see the sequence of CT-slices in the direction of flow.

In a further embodiment, the order of certain operations could be changed. For example, the artery/vessel segmentation could benefit from previously executed masking of skull-bone regions from the 3DRA-generated data set using the CT data. In terms of FIG. 1, this would mean, that blocs ASEG and MSK would be rearranged in the reverser order.

Furthermore, several units can be combined into one unit, such as a processor. The application is not limited to the mentioned radiological methods, but extends to other methods that can be combined in the described fashion as well.

The application is of course not limited to the described or shown embodiments, but generally extends to any embodiment, which falls within the scope of the appended claims as seen in light of the foregoing description and drawings. While a particular feature of the application may have been described above with respect to only one of the illustrated embodiments, such features may be combined with one or more features of other embodiments, as may be desired and advantageous for any given particular application. From the above description of the application, those skilled in the art will perceive improvements, changes and modifications. Such improvements, changes and modifications within the skill of the art are intended to be covered by the appended claims. Any reference signs in the claims do not limit the scope of the application. The term "comprising" is to be understood as not excluding other elements or steps and the term "a" or "an" does not exclude a plurality.

The invention claimed is:

1. System for visualization of biological tissue, comprising:
    a data receiving and processing unit programmed to:
        receive a 3D CT image from a CT scanner which generates the 3D CT image of a selected region of a subject,
        receive a 3D angiography image from a 3D angiography scanner which generates the 3D angiography image of the selected region of the subject,
        register the 3D CT image to the 3D angiography image, segment the 3D angiography image to generate a 3D image of blood vessels and bone tissue, segment the registered 3D CT image to generate a 3D image of bone tissue, subtractively combine the 3D image of blood vessels and bone tissue and the 3D bone tissue image to generate a 3D blood vessel image; and a display unit connected with the data receiving and processing unit which displays at least selected portions of the 3D blood vessel image.

2. The system as claimed in claim 1 further including:

a 3D rendering unit connected with the data receiving and processing unit, the 3D rendering unit projecting the 3D blood vessel image into 2D space to generate a 2D blood vessel projection image;

a frame buffer which buffers the 2D blood vessel projection image, the frame buffer being connected to the display unit to supply the 2D blood vessel projection image thereto for display.

3. The system as claimed in claim 1, wherein the data receiving and processing unit is further programmed to:

filter the 3D angiography image to remove artifacts prior to segmenting the 3D angiography image.

4. The system as claimed in claim 2, further including:

a control unit by which an operator selects corresponding portions of the registered 3D CT image and the 3D blood vessel image and a projection direction, the control unit being connected with the 3D rendering unit to control a projection direction and a portion of the 3D blood vessel image to be projected.

5. The system as claimed in claim 4 further including:

a processor connected with the control unit and the data receiving and processing unit, the processor programmed to:

select a slice of the registered 3D CT image;

render portions of the registered 3D CT image on one side of the selected slice transparent;

perform multi-planar reformatting of the registered 3D CT image with portions rendered transparent in accordance with the selected projection direction to generate a multi-planar reformatted image; and supplying the multi-planar reformatted image to the frame buffer for display on the display unit.

6. The system as claimed in claim 5 wherein the processor is programmed to:

combine the multi-planar reformatted image and the projected portion of the 3D blood vessel images.

7. A method for visualization of biological tissue comprising:

acquiring from a first diagnostic scanner a first data set corresponding to a three-dimensional data acquisition based on a first acquisition method;

acquiring from a second diagnostic scanner a second data set corresponding to three-dimensional data acquisition based on a second acquisition method;

registering the first and second data sets including shifting, scaling, and rotating the first data set such that congruence in regard to size, position, and orientation between the first and second data sets is achieved;

segmenting bone information from the shifted, scaled, and rotated first data set to generate a mask data set;

segmenting blood vessel and bone information from the second data set;

merging the mask data set and the segmented second data set to generate a blood vessel data set;

projecting the artery/blood vessel data set onto a 2D plane; and converting the projection of the blood vessel data set onto a 2D image plane into a human readable display for analysis by human users.

8. The method as claimed in claim 7, wherein acquiring the first data set includes:

using a computer tomographic (CT) scanner to conduct a CT scan of a selected region of a subject such that the first data set is a 3D CT data set.

9. The method as claimed in claim 8, wherein acquiring the second data set includes:

using a three-dimensional rotational angiographic (3DRA) scanner to generate a 3DRA scan of the selected region of the subject such that the second data set is a 3DRA data set.

10. The method as claimed in claim 7, further including:

filtering artifacts from the second data set prior to registering the first and second data sets.

11. The method as claimed in claim 7 further including:

obtaining sectional views of the first data set, and/or the second data set on a corresponding preselected geometrical plane.

12. The method as claimed in claim 11 further including:

rendering data in at least one of the sectional views transparent based on location and characteristic; and combining the sectional views of the first and second data sets.

13. The method as claimed in claim 12 further including:

projecting the combined sectional views along a predefined path, onto a 2D plane; and displaying the combined sectional views projected onto the 2D plane on a display unit.

14. A system for visualization of blood vessels and bone including:

a computer tomography (CT) device which obtains a 3D CT image data set including information as to three-dimensional locations and as to physical properties in the locations;

a three-dimensional rotational angiography (3DRA) device which obtains a 3DRA image data set including information as to three-dimenstional locations and as to physical properties in the locations;

a bone segmentation (SSEG) unit which segments the 3D CT data set to isolate bone information from the 3D CT data set;

an artery segmentation unit (ASEG) operative to receive the 3DRA data set and output a 3D blood vessel and bone data set;

a masking unit (MSK) operative to merge the outputs of the artery segmentation unit (ASEG) and the bone segmentation unit (SSEG) to remove bone from the 3D blood vessel and bone data set to generate a 3D blood vessel data set; and a display device which displays at least a portion of the 3D blood vessel data set.

15. The system as claimed in claim 14 further including:

a volume slice control unit (VSC) which breaks the registered 3D CT data set into slices or small volumes, in simple geometric shapes easily analyzed by human users, and controls a position, orientation, size, partial transparency, and other properties and supplies the slices or small volumes to the display device for display.

16. The system as claimed in claim 14 further including:

a rendering unit (SREN) which renders volume slices of the registered 3D CT image data set partially transparent, the partially transparent volume slices being supplied to the display device to be displayed with the blood vessel data set.

* * * * *